(12) United States Patent
Lehane et al.

(10) Patent No.: US 10,328,427 B2
(45) Date of Patent: Jun. 25, 2019

(54) ASSAY DEVICE

(71) Applicant: SPD Swiss Precision Diagnostics GMBH, Geneva (CH)

(72) Inventors: Kieran Andrew Lehane, Bedford (GB); Steven Hart, Bedford (GB)

(73) Assignee: SPD SWISS PRECISION DIAGNOSTICS GMBH, Geneva (CH)

( * ) Notice: Subject to any disclaimer, the term of this patent is extended or adjusted under 35 U.S.C. 154(b) by 370 days.

(21) Appl. No.: 15/101,329

(22) PCT Filed: Dec. 4, 2014

(86) PCT No.: PCT/EP2014/076643
§ 371 (c)(1),
(2) Date: Jun. 2, 2016

(87) PCT Pub. No.: WO2015/082646
PCT Pub. Date: Jun. 11, 2015

(65) Prior Publication Data
US 2016/0303558 A1    Oct. 20, 2016

(30) Foreign Application Priority Data

Dec. 4, 2013  (GB) .................................. 1321430.9

(51) Int. Cl.
*B01L 3/00*    (2006.01)
*G01N 33/543*  (2006.01)
(Continued)

(52) U.S. Cl.
CPC .......... *B01L 3/5023* (2013.01); *G01N 33/548* (2013.01); *G01N 33/549* (2013.01);
(Continued)

(58) Field of Classification Search
None
See application file for complete search history.

(56) References Cited

U.S. PATENT DOCUMENTS 5,837,546 A * 11/1998 Allen ................. G01N 21/8483
                                                          436/169
6,261,519 B1    7/2001 Harding et al.
(Continued)

FOREIGN PATENT DOCUMENTS

| CN | 1615441 A | 5/2005 |
| CN | 1902489 A | 1/2007 |

(Continued)

*Primary Examiner* — Changhwa J Cheu
(74) *Attorney, Agent, or Firm* — David Halstead; Erik Huestis; Foley Hoag LLP (57) ABSTRACT

The present invention provides an assay device for detecting an analyte in a fluid sample, comprising: a sample receiving member (1), which is fluidically connected to at least two components (2, 3) defining an assay flow path, at least one of which is a detection member (3) comprising an analyte detection zone (31); and a sample detection element (13) adapted to detect fluid at a particular point along the assay flow path. The present invention also provides the use of the assay device of the invention for indicating sample sufficiency when the assay device is exposed to a fluid sample and for indicating to a user after sampling that the device has failed due to insufficient sampling, and a method of alerting a user to the fact that a sufficient sample has been applied to an assay device of the invention.

28 Claims, 4 Drawing Sheets

(51) Int. Cl.
*G01N 33/558* (2006.01)
*G01N 33/548* (2006.01)
*G01N 33/549* (2006.01)
*G08B 5/36* (2006.01)
*G08B 21/18* (2006.01)

(52) U.S. Cl.
CPC ..... *G01N 33/54366* (2013.01); *G01N 33/558* (2013.01); *G08B 5/36* (2013.01); *G08B 21/182* (2013.01); *B01L 2200/143* (2013.01); *B01L 2300/0645* (2013.01); *B01L 2300/0825* (2013.01)

(56) References Cited

U.S. PATENT DOCUMENTS

| | | |
|---|---|---|
| 6,998,273 B1 | 2/2006 | Fleming et al. |
| 7,239,394 B2 | 7/2007 | Sharrock et al. |
| 7,315,378 B2 | 1/2008 | Phelan et al. |
| 7,317,532 B2 | 1/2008 | Sharrock et al. |
| 7,338,639 B2 | 3/2008 | Burke et al. |
| 7,597,793 B2 | 10/2009 | Burke et al. |
| 7,879,624 B2 | 2/2011 | Sharrock |
| 8,606,528 B2 | 12/2013 | Sharrock |
| 2002/0155029 A1 | 10/2002 | Mink et al. |
| 2002/0175075 A1 | 11/2002 | Deng et al. |
| 2004/0152208 A1 | 8/2004 | Hutchinson |
| 2004/0248322 A1 | 12/2004 | Charlton |
| 2005/0023137 A1* | 2/2005 | Bhullar ............. G01N 27/3272 204/403.1 |
| 2005/0023152 A1 | 2/2005 | Surridge et al. |
| 2005/0221504 A1 | 10/2005 | Petruno et al. |
| 2006/0008896 A1 | 1/2006 | Nazareth et al. |
| 2008/0145949 A1 | 6/2008 | Song et al. |
| 2009/0157023 A1 | 6/2009 | Song et al. |
| 2011/0027901 A1 | 2/2011 | Gaster et al. |
| 2011/0184264 A1 | 7/2011 | Galasso et al. |
| 2012/0083044 A1 | 4/2012 | Sturman et al. |
| 2012/0109011 A1 | 5/2012 | Cogan et al. |

FOREIGN PATENT DOCUMENTS

| | | | |
|---|---|---|---|
| CN | 102141566 A | 8/2011 | |
| CN | 102462512 A | 5/2012 | |
| EP | 291194 A1 | 11/1988 | |
| EP | 2 602 620 A1 | 6/2013 | |
| JP | 2010/217074 A | 9/2010 | |
| WO | 9746868 A1 | 12/1997 | |
| WO | WO-03/058245 A1 | 7/2003 | |
| WO | WO-2004/003559 A1 | 1/2004 | |
| WO | 2008139324 A2 | 11/2008 | |
| WO | 13083686 A1 | 6/2013 | |
| WO | 2013/178739 A1 | 12/2013 | |
| WO | WO-2013178739 A1 * | 12/2013 | ........... G01N 33/525 |
| WO | WO-2014/158845 A1 | 10/2014 | |
| WO | WO-2014/158850 A1 | 10/2014 | |

* cited by examiner

ASSAY DEVICE

The present invention relates to an assay device which gives an indication to the user when a sufficient amount of sample has been applied to the device for the device to function adequately and produce an accurate result. The assay device also provides assurance to the user that they have performed the sampling and hence performed the test correctly.

Various diagnostic products are known which analyse a fluid sample, such as urine or blood, to determine the presence or amount of one or more analytes. These may be small, handheld devices, which are used by applying the biological sample to an absorbent component; the devices are configured to subsequently convey the fluid along a flow path to an assay test zone without needing any significant gravitational encouragement, e.g. by applied pressure, where a reaction or binding event takes place to afford the assay result.

An example of a device of this nature is the lateral flow type assay device described in EP 0,291,194. This document discloses an immunoassay device comprising a type of sample application region (or sample receiving member) known as a wick, which overlaps and is fluidically connected to a porous carrier containing a reagent zone bearing a mobilisable labelled specific binding reagent for an analyte. Downstream, an unlabelled specific binding reagent for the analyte is immobilised in a test zone or analyte detection zone. The user performs the single step of applying liquid sample to the wick, and the sample is subsequently conveyed along the flow path by capillary action. The device is designed to enable the controlled release of the mobilisable labelled reagent by the sample. Any analyte in the sample will then interact with the released labelled specific binding reagent to form a labelled complex, which is carried to the test zone where it forms a "sandwich" complex with the immobilised unlabelled binding reagent. The label, which may be a coloured particle, thereby becomes concentrated and observable in the test zone to indicate the presence and/or amount of analyte in the sample. The test zone can be directly observed by the user to determine the test result in what are known as visually read tests. However in digital tests, the test zone can be measured by an optical or other reading system and the result presented on a display, such as a LCD display. See, for example, U.S. Pat. No. 7,879,624.

The correct functioning of these assays is reliant upon the application of a sufficient volume of sample to the device by the user. On using such tests there are incidences where the user provides an insufficient volume of liquid sample, for example urine. This can lead to failure of the assay because the test sample does not reach the assay reagents which are positioned downstream of the wick along the flow path. An insufficient volume of sample can influence the flow rate of the sample along the flow path such that improper or uncontrolled mobilisation of the mobilisable labelled reagent (rate and total quantity released) impacts the performance of the test affecting its ability to deliver the correct result. A correct result is defined by the delivery of a positive or negative result, for example Pregnant or Not Pregnant to the user rather than a void result informing the user to re-test due to a failed device.

An insufficient sample volume applied to a visually read device can manifest itself in a number of ways, for example as a device which produces no test and control lines, no control line as well as partly formed test and/or control lines. Various test and control line formations may be accompanied by a smear of mobilisable label in the read window, which is the area of the device which is visually observed by the user or is measured by an optical or other reading system to interpret the test result. This leads to confusion in interpreting the result as well as user frustration which ultimately leads to a wasted test device since the test has to be repeated. Digital test devices can comprise numerous monitoring means which track events such as wetting on the test device from the onset of applying the urine sample to the test. Clearblue single use disposable digital tests (Swiss Precision Diagnostics GmbH) for instance have a "wake up" period defined as the time taken for current to start flowing through the device from the point of application of the urine sample to the sample receiving member and the flow of sample reaching a pair of electrodes which are in contact with the sample receiving member. This event effectively "wakes" the digital test up from a standby mode. Once woken, such devices continue to monitor the flow of sample along the flow path by measuring the time for the solvent front to reach one or more optical sensors arranged along the flow path. An onboard digital processor has pre-defined limits for the time taken for the flow to reach the sensor(s) allowing the determination of improper flow to indicate a failed device. Such measurement systems monitor the flow of sample along the flow path and can also determine the direction of flow; they do not necessarily reduce the incidence of an insufficient volume of sample being applied to the device. Wastage of a test device through insufficient sampling can thus still occur.

Accordingly, the user is generally instructed to take care to apply a certain volume of sample e.g. by holding the wick in their urine stream for 5 seconds or by dipping the wick up to a certain distance in urine collected in a container for 5 to 20 seconds. The sampling time can of course vary for different test devices.

Whilst sampling onto such devices is largely not an issue, often the user is a naïve or an infrequent user of this type of assay and is expected to interpret the procedure for performing the assay from reading instructions and observing diagrams which are provided with the assay. Unfortunately, however, some users do not always comply with the instructions, for instance due to misinterpreting them or not reading them at all in their eagerness to use the device.

The issue of insufficient sampling is particularly relevant to urine sampling. When detecting analyte in a urine sample, for example when testing for pregnancy, the user may prefer to apply their urine to the sample application area directly from their urine stream ("midstream sampling") rather than collect their urine in a container first. In practice they may experience difficulties in controlling the direction of their urine stream onto the wick and, especially for women (bearing in mind their anatomy), being able to see what they are doing when midstream sampling. Current devices require the user to collect the urine from the urine stream for a number of seconds, typically between 5 and 10 seconds. Individuals may choose to use a timer, for example a watch, to help time the collection of urine on the device, thus adding another activity they have to contend with at an anxious time. Others may choose not to use a timer and rely on counting themselves for a period of time. The perception of time can vary widely between individuals adding to the variability in the time the device is exposed to the urine. This is further varied by the device not being exposed to urine stream for a proportion of this time due to the variability in the direction of the urine stream and the difficulty in observing the collection of urine during midstream sampling.

Provision of an insufficient urine sample is therefore possible, for example if the user does not adequately time the sampling event. This applies whether the user is dipping the wick of the device in a container of collected urine or is midstream sampling. Trials have shown the urine stream and the position of the wick as it is held within the urine stream can vary, thus influencing the total volume of urine applied to the wick. Also the user may not dip the wick to the required extent in a container of collected urine influencing the volume of urine collected by the wick causing insufficient sampling.

Efforts have been made to assist the users of such assays by providing in the assay device means for indicating that a sufficient amount of sample has been obtained.

For example, a known assay device as described in EP 0,291,194 has a control zone downstream from the test zone, where the formation of a line at the control zone indicates to the user that the sample has flowed past the test zone and so it is likely that enough sample has been applied. The user is instructed to reject the test as invalid if the control line fails to develop. However, because the user must wait the required time to see if the control line forms (typically several minutes), they do not receive any feedback during the sampling event itself, so the test may be wasted if undersampling occurs. Also, the absence of a control line does not inform the user that undersampling must have occurred; it could be due to degradation of reagents during storage of the device.

There is therefore a need in the art for an assay device such as a lateral flow assay device that indicates that sufficient sample has been applied, preferably by giving feedback to the user during the sampling event, and for urine sampling preferably in a way that is easily recognised by the user without having to remove the wick from the urine stream. This feedback is important as it reassures the user that they are following the correct steps in performing the test and that the test is functioning in its intended manner. Users of such devices may be emotional in anticipation of a negative or positive result; hence any reassurance that they are performing the test correctly is of value.

The present inventors have now devised a way of indicating that sufficient sample, in particular a sample of urine, has been applied to an assay device and in particular a lateral flow device, by giving feedback to the user during the sampling event, and in a way that is easily recognised by the woman without having to remove the wick from her urine stream.

Accordingly, in a first aspect the present invention provides an assay device for detecting an analyte in a fluid sample, comprising:
  a sample receiving member (1), which is fluidically connected to at least two components (2, 3) defining an assay flow path, at least one of which is a detection member (3) comprising an analyte detection zone (31); and
  a sample detection element (13) adapted to detect fluid at a particular point along the assay flow path.

In one embodiment, the sample detection element (13) is in contact with the assay flow path. In one embodiment, the sample detection element (13) is an electrode or a pair of electrodes (5, 6).

Embodiments will now be described, by way of example, with reference to the accompanying drawings in which.

The device architecture used in FIGS. 4 to 8 may be in accordance with FIG. 1 or 2.

By "assay flow path" is meant the path along which the sample fluid is intended to flow during performance of the assay. The assay flow path is made up of at least two components. Typically, the components are fluidically connected. Typically, the components at least partially overlap each other. The assay flow path is typically made up of two components, for example two fluidically connected strips that partially overlap each other. The assay flow path is also referred to herein as the "test strip".

When referring to the location of a component in the assay flow path, "upstream" means that the component is closer to the sample receiving member. Conversely, "downstream" means that the component is further away from the sample receiving member.

The sample receiving member is capable of receiving a fluid sample, typically a liquid sample and of transferring the sample to the assay flow path. The sample receiving member may act as a sample capture means, and may be present in a sample receiving portion of the assay device. The sample receiving member may be an elongated strip. It may project from a housing that encloses the assay flow path. In the present invention, the sample receiving member is typically made of a porous material. The sample receiving member is typically non-swellable. In an embodiment, the sample receiving member is macroporous. In an embodiment, the device is adapted to transfer the sample from the sample receiving member to the assay flow path without user-applied force. Preferably, the materials of the sample receiving member and components of the assay flow path are selected such that the sample is transferable from the sample receiving member to the start of the assay flow path by capillary action only.

The sample receiving member may comprise one or more different porous materials. It may be fibrous or non-fibrous. Suitable porous materials include glass fibre, cellulose, nitrocellulose, paper, silica, porous synthetic polymers such as sintered PET, and material comprising polyester, nylon, cotton, mono-component fibre combinations thereof, or bi-component fibre combinations thereof. The porous material may be a woven or a non-woven material. In one embodiment, the sample receiving member comprises polyester fibres and/or nylon fibres.

In an embodiment, the sample receiving member is a wick. The wick may comprise a material of relatively high capacity and high capillarity through which liquid can flow relatively easily. This may be relative to the other components of the assay flow path. This allows the wick to rapidly absorb a volume of sample liquid that is applied to the device, and also allows sufficient volume of sample liquid to be transferred easily to the assay flow path.

The sample that is applied to the assay device is a fluid. The sample may naturally be a liquid, or may be a solid that has been pre-treated so as to be provided in liquid form before application to the device. For example, a solid sample such as faeces can be dissolved in a suitable solvent before being applied to the device. Alternatively, a liquid sample may be treated with another liquid (such as water or an aqueous solution) to alter its viscosity and/or increase its volume before being applied to the device. The sample can be derived from any source and may be a bodily fluid, including blood, serum, plasma, saliva, sputum, ocular lens liquid, sweat, urine, milk, ascites liquid, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions, and amniotic liquid. Depending upon the analyte of interest, other samples may be contemplated such as ones from industrial, environmental or agricultural sources.

In an embodiment, the sample is aqueous. In an embodiment, the sample has a viscosity of ≤2 mPa·s, ≤1.5 mPa·s, or ≤1 mPa·s at 25° C. In an embodiment, the sample is urine or a diluted bodily fluid.

During use of the device, the sample is conveyed along the assay flow path in which one or more reagents for the assay are found. The reagent(s) will vary according to the type of assay. The reagent(s) may interact with the analyte to form a detectable product, for example via a simple binding reaction to form an analyte-reagent complex, or via a chemical reaction.

The assay reagents may comprise mobilisable and immobilised assay reagents; the mobilisable reagents may be pre-deposited on the components defining the assay flow path in a dry form. The "analyte detection zone", where a signal is formed indicating the presence and/or amount of analyte, may contain the immobilised assay reagents, and the mobilisable assay reagents may be initially provided in a zone ("mobilisable reagent zone") upstream from the analyte detection zone. In the case where the assay comprises a sandwich assay, the mobilisable reagent zone may bear a mobilisable labelled binding reagent for the analyte and, downstream from this, the analyte detection zone bears immobilised non-labelled binding reagent for the analyte. Of course, other assay formats such as a competition assay or inhibition assay are also possible, known to the skilled person and included within the scope of the invention. Another example is where the analyte is an enzyme, which is capable of cleaving the assay reagent to produce a cleavage product that is subsequently detected. In some embodiments, the cleavage product may not be directly detectable; instead the cleavage product can be subsequently involved in other reactions which eventually lead to a product(s) that are detected.

The components defining the assay flow path may also contain one or more control reagents, which may be used in the conventional fashion to provide an indication at a "control zone" that the assay has run correctly. Accordingly, in one embodiment the assay flow path further comprises a control zone. For instance, mobilisable labelled control reagents may be provided at an upstream location in the assay flow path (e.g. in the mobilisable reagent zone), with immobilised control reagents in the control zone. The mobilisable control reagents may bind to the immobilised control reagents, and so accumulation of the label in the control zone affords a signal that the assay has run correctly. The mobilisable labelled test reagents may bind to the immobilised control reagents to form the control zone. Typically, the control zone is located downstream from the analyte detection zone.

The assay flow path may be defined by a plurality of fluidically connected components. In one embodiment, the mobilisable reagent zone may be provided on a first material (which may be a so-called "conjugate pad"), and the analyte detection zone may be provided on a downstream, fluidically connected, second material (which may be nitrocellulose).

The components defining the assay flow path may comprise any material capable of allowing the sample to flow from the sample receiving member to the assay reagent(s). The assay device may be configured as a lateral flow device, and the components may comprise a porous, fibrous or bibulous carrier.

In an embodiment, the components comprise a plurality of fluidically connected porous carriers. The porous carriers may comprise any material suitable for conveying the sample to the assay reagent(s). The wicking rate of the sample along the assay flow path is preferably slower than the wicking rate of the sample through the sample receiving member.

Examples of the porous carrier materials include glass fibre, cellulose, nitrocellulose, paper, silica, porous synthetic polymers such as sintered PET, and material comprising polyester, nylon, cotton, mono-component fibre combinations thereof, or bi-component fibre combinations thereof. The porous carrier materials may be a woven or a non-woven material.

In an embodiment, the porous carriers comprise glass fibre and/or nitrocellulose. In an embodiment, the components defining the assay flow path comprise a glass fibre pad on which the mobilisable reagent zone is located, and a nitrocellulose strip on which the analyte detection zone is located, the glass fibre pad being fluidically connected to and upstream of the nitrocellulose strip.

At least a portion of the sample receiving member may overlap the upstream component of the assay flow path. Alternatively, they may be in end-to-end contact.

The assay device may further comprise a sink pad located downstream from all the assay reagents and any control reagent(s) present in the assay flow path, typically at the terminus of the assay flow path. The sink pad encourages continued flow of the sample along the assay flow path, by wicking sample from the other, upstream components defining the assay flow path and retaining it within the sink pad. The sink pad may comprise any suitable absorbent or bibulous material as is known in the art, such as cellulose, cotton and/or glass fibre.

The assay device of the invention includes a sample detection element that is adapted to detect fluid at a particular point along the assay flow path. The point along the assay flow path at which fluid is detected will be dictated by the location of the sample detection element.

In some embodiments, the sample detection element is in contact with the assay flow path. In these embodiments, fluid is detected when flows along the assay flow path and comes into contact with the sample detection element.

In one embodiment, the sample detection element is in contact with the first component of the assay flow path. In one embodiment, where the first component and the second component of the assay flow path at least partially overlap, the sample detection element is in contact with the first component of the assay flow path in the area where the first component and second component overlap. In another embodiment, where the first component and the second component of the assay flow path at least partially overlap, the sample detection element is in contact with the first component of the assay flow path in the area where the first component and second component do not overlap. In this embodiment, if the first component of the assay flow path and the sample receiving member overlap, the sample detection element is typically in contact with the first component of the assay flow path in the area where the first component of the assay flow path and the sample receiving member do not overlap. In another embodiment, the sample detection element is in contact with the second component of the assay flow path.

The sample detection element may be any suitable means of detecting the presence of sample in the location where the element resides; the detection being performed either solely by the element itself or in conjunction with another component of the device. In some embodiments, the sample detection element itself is adapted to indicate to the user that the presence of sample at the sample detection element has been detected. In some embodiments, the presence of sample at the sample detection element is indicative that a sufficient amount of sample has been obtained. In other embodiments, the presence of sample at the sample detection element triggers a further event or series of events which is/are indicative that a sufficient amount of sample has been obtained.

In one embodiment, the sample detection element comprises a visual sensing system. This may be a chemical sensing system which may comprise a reagent which changes colour in response to an inherent property of the sample, e.g. water content, pH, chemical component (other than the analyte which is being tested for), temperature (if the sample is a recently obtained bodily fluid). Such a reagent is referred to herein as a colour change reagent. Compounds which change colour upon hydration are well known to the skilled person and include cobalt (II) chloride, copper (II) sulphate. The reagent may be supported on a substrate e.g. paper. The colour change may be observable visually through a window in the housing of the device. The colour change may be measurable or visible to the eye through a window in the housing of the device.

In some embodiments, the sample detection element consists of a chemical sensing system comprising one or more colour change reagents, i.e. no other components are present in the chemical sensing system. For example, the chemical sensing system can comprise one or more colour change reagents, together with one or more buffers, detergents and/or proteins, but no other components. In one embodiment, the sample detection element is a pH indicator, such as pH indicator paper.

In another embodiment, the sample detection element comprises an optical sensing system. For instance, the colour change of the sensing system described above may be detected using appropriate illumination and detection elements such as light emitting diodes and photodetectors. Such detection elements may be used to detect changes in the optical properties of the sample detection element, for example the change in the transmission of light on the sample detection element, for example when going from the dry to the wet state. In these embodiments, the sample detection element is not in contact with the assay flow path.

In one embodiment, the sample detection element is non-absorbent.

In another embodiment, the sample detection element comprises an electrode. In one embodiment, the sample detection element is a pair of electrodes. In another embodiment, the sample detection element is a single electrode.

In one embodiment, the assay device of the present invention therefore includes a pair of electrodes (i.e. two electrodes) in contact with the assay flow path. These electrodes are shown as components 5 and 6 in the Figures herein. In some embodiments, the assay device includes a single pair of electrodes, i.e. only two electrodes.

The aim of this configuration of the assay device of the invention is that when sample fluid, such as urine, flows along the assay flow path and arrives at the point in the assay flow path that is in contact with the pair of electrodes, the sample fluid acts as an electrolyte bridge to complete an electrical circuit in which the electrodes are comprised. Current then flows in the electrical circuit (including a battery) to power an indication system, which provides an indication that sample fluid has been detected at the point in the assay flow path that is in contact with the pair of electrodes. An indication can then be provided to the user that a sufficient amount of sample has been applied. The indication of sample sufficiency can be provided either directly or indirectly, as described herein. Preferably, the indication method provides immediate feedback to the user during sampling itself, so that they can ensure sufficient sample is applied. This is particularly useful in relation to midstream sampling of urine. Alternatively, the indication method provides feedback to the user after sampling that the test should be rejected because of undersampling. This provides valuable feedback to the user, making them aware that undersampling was the cause of device failure. On testing with another device the user will be more aware of the importance of sampling correctly.

In one embodiment, the pair of electrodes are in contact with the first component of the assay flow path. For example, where the mobilisable assay reagent(s) are borne by a first porous material, and the immobilised assay reagents are borne by a fluidically connected second porous material, the pair of electrodes are in contact with the first porous material. In an alternative embodiment, the pair of electrodes are in contact with the second component of the assay flow path. For example, where the mobilisable assay reagent(s) are borne by a first porous material, and the immobilised assay reagents are borne by a fluidically connected second porous material, the pair of electrodes are in contact with the second porous material.

In one embodiment, where the first component and the second component of the assay flow path at least partially overlap, the sample detection element (such as a pair of electrodes) is in contact with the first component of the assay flow path in the area where the first component and second component overlap. For example, where the first porous material and the second porous material at least partially overlap, the sample detection element (such as a pair of electrodes) is in contact with the first porous material in the area where the first porous material and the second porous material overlap. In this embodiment, when the sample detection element is a pair of electrodes they may also be in contact with the second component of the assay flow path, for example by means of piercing all the way through the first component of the assay flow path such that the electrodes also contact the second component of the assay flow path.

When the first porous material is a conjugate pad and the second porous material is nitrocellulose, this arrangement is particularly advantageous, as is the embodiment where the sample detection element (such as a pair of electrodes) is in direct contact with the second porous material, i.e. the nitrocellulose. This is because once the sample fluid has reached the nitrocellulose the assay device will run correctly since the nitrocellulose has a greater capillary pull than the conjugate pad as well as the sample receiving member and so will draw sample fluid from those components of the assay device.

In another embodiment, where the first component and the second component of the assay flow path at least partially overlap, the sample detection element (such as a pair of electrodes) is in contact with the first component of the assay flow path in the area where the first component and second component do not overlap. In this embodiment, if the first component of the assay flow path and the sample receiving member overlap, the sample detection element (such as a pair of electrodes) is typically in contact with the first component of the assay flow path in the area where the first component of the assay flow path and the sample receiving member do not overlap.

The pair of electrodes consists of two electrodes. In some embodiments, the pair of electrodes consists of an anode and a cathode. The pair of electrodes typically consists of two elongated strips, but can be of any suitable shape or size.

In one embodiment, the two electrodes are located on the same side of the assay flow path. In this embodiment, the two electrodes can be elongated strips that are approximately in parallel to each other. In another embodiment, one of the electrodes is located on one side of the assay flow path and the other electrode is located on another side of the assay flow path. The electrodes do not necessarily need to be parallel to each other and can be of different shapes and sizes.

The electrodes can be made of any suitable material. Typically, the electrodes are made of a metal, for example steel, copper, silver, lead or zinc. Alternatively, the electrodes are made of a non-metal, for example carbon. Both electrodes may be made from the same material or they may be made from two different respective materials. In some embodiments, the surface of one or both of the electrodes can be treated, for example with a hydrophilic layer, to help wetting.

The pair of electrodes (i.e. the two electrodes) can be placed in contact with the assay flow path using any suitable means. This will of course depend on the shape and dimensions of the electrodes as well as the characteristics of the component(s) of the assay flow path with which the electrodes are in contact. Typically, the electrodes are in surface contact with the appropriate component(s) of the assay flow path. In one embodiment, the electrodes are spring loaded to hold them in contact with the appropriate component(s) of the assay flow path. In other embodiments, the electrodes may project into or pierce one or more of the components of the assay flow path. For example, in one embodiment, where the first component and the second component of the assay flow path at least partially overlap, the pair of electrodes may project into or pierce through the first component of the assay flow path and make contact with the second component of the assay flow path, or vice versa. In this embodiment, the pair of electrodes, having pierced the first component of the assay flow path, may also pierce the second component of the assay flow path or may just make surface contact with the second component of the assay flow path. In one embodiment, the electrodes can be impregnated or formed as part of the component(s) of the assay flow path, i.e. they are present within the structure of that component. In one embodiment, the electrodes are part of a conductive mesh that is in contact with or present within the structure of one or more of the component(s) of the assay flow path. For example, one or more components of the assay flow path may be overlaid onto such a conductive mesh.

In some embodiments, such as those described above, detection of sample fluid at the pair of electrodes that are in contact with the assay flow path and therefore the flow of current from the battery is itself indicative that a sufficient amount of sample has been applied. In other embodiments, the pair of electrodes that are in contact with the assay flow path are used in combination with other elements of the assay device to indicate sample sufficiency.

It is known in the art to use the change in impedance between electrodes to "wake up" assay devices of the lateral flow type from a standby mode. This is useful since the shelf life of such products can be up to a number of years, and the battery needs to be preserved until the time when the device is ready to be used. In some such devices, a pair of electrodes is in contact with the sample receiving member. When sample fluid is applied to the sample receiving member it flows along the sample receiving member and at the point at which it meets the electrodes, the sample fluid acts as an electrolyte bridge to complete an electrical circuit in which the electrodes are comprised. This then causes current to flow from a battery in the circuit, and the point at which current begins to flow from the battery in such devices is referred to herein as "wake up" of the device. The electrodes used to "wake up" such assay devices are also referred to herein as "auto-starts". Once woken, the device can perform the necessary checks on its software and hardware in anticipation of the sample flowing along the porous carrier in readiness of making the necessary analysis. Assay devices can also be induced to "wake up" by means of a mechanical switch or by using a test reactive to light, such that the device is woken up upon removal from the pouch in which it is stored or by removal or displacement of a cap. Assay devices including any such methods of causing "wake up" together with the indicator of sample sufficiency are within the scope of the present invention. In some embodiments, "wake up" of the device is measured using a DC technique. For example, a positive voltage can be applied through a resistor and if the resistance between the two electrodes (autostarts) drops this causes a current to flow though the resistor and the voltage after the resistor to drop. The falling of this voltage then "wakes up" the device.

In one embodiment of the invention, the assay device further comprises a second pair of electrodes that are in contact with the sample receiving member. These electrodes are shown as components 7 and 8 in the Figures herein. This arrangement can be used in combination with any type of sample detection element, as described herein. In the embodiments where the assay device comprises a second pair of electrodes (7,8) and also a pair of electrodes (5,6), the pair of electrodes (5,6) are referred to herein as the first pair of electrodes.

Thus, in one embodiment, the present invention provides an assay device for detecting an analyte in a fluid sample, comprising:
 a sample receiving member (1), which is fluidically connected to at least two components (2, 3) defining an assay flow path, at least one of which is a detection member (3) comprising an analyte detection zone (31); and
 two pairs of electrodes (5, 6) (7,8), wherein the first pair of electrodes (5,6) are in contact with the assay flow path and the second pair of electrodes (7,8) are in contact with the sample receiving member.

The features of the second pair of electrodes are as described herein for the first pair of electrodes.

The second pair of electrodes can be placed in contact with the sample receiving member using any suitable means. This will of course depend on the shape and dimensions of the electrodes as well as the characteristics of the sample receiving member being used. Typically, the electrodes are in surface contact with the sample receiving member. In other embodiments, the electrodes may project into or pierce the sample receiving member.

In one embodiment, the assay device is set up to "wake up" when sample fluid contacts the second pair of electrodes, but not to provide an indication of sample sufficiency until the sample has flowed to one or more of the components defining the assay flow path, as defined by the location of the sample detection element (such as the first pair of electrodes) on the assay flow path, as described above. In one example, the first pair of electrodes is located on the conjugate pad in the area where the conjugate pad overlaps the nitrocellulose. In another example, the first pair of electrodes is located on the conjugate pad in the area where the conjugate pad does not overlap the nitrocellulose. In another example, the first pair of electrodes is located on the nitrocellulose. Once sample fluid has reached those electrodes, current flows into a separate circuit which provides an indication that a sufficient amount of sample has been applied, as described above.

In another such embodiment, an indication of sample sufficiency is given by monitoring the time elapsed between "wake up" of the device (as indicated by current flowing from the second pair of electrodes caused by sample fluid contacting the second pair of electrodes) and sample fluid arriving at the sample detection element (such as the first pair of electrodes located on the assay flow path, in which case the sample fluid arriving at the first pair of electrodes will be indicated by current flowing from the first pair of electrodes). In one example, the sample detection element such as the first pair of electrodes is located on the conjugate pad, upstream of the nitrocellulose.

In these embodiments, a timer can be used to monitor the amount of time elapsed between wake up and indication of sample sufficiency, with an indication being given to the user if a sufficient amount of sample has been obtained in a given time. This has the advantage that the user is alerted to stop sampling earlier, hence reducing the total time of sampling and avoiding the possibility of the user flooding the device (i.e. applying too much sample, which can also cause the device to fail). Current devices do not have any means of indicating when sufficient sample has been applied to the device. On midstream sampling the user is instructed to hold the device in the urine stream for a defined period of time. The user may continue sampling beyond the instructed period of time which can lead to an excessive quantity of sample on the device causing improper flow of the sample along the flow path, known as flooding.

In one embodiment, an indication can be given to the user that a sufficient sample has not been obtained in a given time. The aim of such an indication would be to alert the user to be more vigilant about the sampling procedure when carrying out a subsequent assay.

In some embodiments, the assay device comprises further electrode pairs in addition to the two pairs of electrodes (5,6)(7,8). Such further electrode pairs can be located, for example, between the two pairs of electrodes (5,6) and (7,8) or further downstream of the pair of electrodes (5,6) along the assay flow path.

In one embodiment, the assay device of the invention comprises an indication system adapted to indicate that sufficient sample has been applied. As described herein, this can be a result of sample fluid arriving at the sample detection element, such as a first pair of electrodes located on the assay flow path, for example a first pair of electrodes located in the area where the conjugate pad overlaps the nitrocellulose or located on the conjugate pad in the area where the conjugate pad does not overlap the nitrocellulose or located on the nitrocellulose itself, or as a result of a predetermined time being elapsed between "wake up" of the device and sample fluid arriving at the sample detection element, such as a first pair of electrodes, for example a first pair of electrodes located on the conjugate pad.

The indication system can indicate that sufficient sample has been applied by any suitable method known in the art. The indication method could for example be visual (e.g. optical), aural (e.g. using a piezoelectric sounder) or tactile (e.g. vibrations created in the handle of the device). Optical methods include using LEDs or an LCD screen on which an icon or other message appears once a sufficient amount of sample has been applied to the device. Alternatively, a backlit LCD screen could be used which changes colour to indicate to the user that a sufficient amount of sample has been applied to the device. When the indication method includes an LED, the LED is typically located at the downstream (distal) end of the assay device so that the light is easily visible to the user when carrying out the assay.

Indication methods for example indication by sound or vibration (indirect viewing methods) are preferable for use in midstream sampling, since these methods allow the user to continue holding the device in the urine stream until an indication of sample sufficiency is apparent. Conversely, direct viewing methods generally require the user to bring the device out of the urine stream to visually inspect the status of the sample sufficiency indicator. The device may need to be returned to the urine stream if insufficient sample has been applied to the device.

In a second aspect, therefore, the present invention provides the use of an assay device of the invention for indicating sample sufficiency when the assay device is exposed to a fluid sample, for example when the device is held in the urine stream of a user or is dipped into a urine sample held in a container. In a related aspect, the invention also provides a method of alerting a user to the fact that a sufficient sample has been applied to an assay device of the invention, comprising (a) exposing an assay device of the invention to a fluid sample; and (b) alerting the user to the fact that a sufficient sample has been obtained. In one embodiment, the invention provides a method of alerting a user to the fact that a sufficient sample has been obtained when mid-stream urine sampling, comprising: (a) holding an assay device of the invention in the urine stream of a user; and (b) alerting the user to the fact that a sufficient sample has been obtained, whilst the user continues to sample from the urine stream. In these aspects of the invention, the assay device comprises an indication system to alert the user to the fact that a sufficient sample has been obtained. The user is typically a female user as the assay device is typically a pregnancy test. In a related aspect, the present invention provides the use of an assay device of the invention for indicating to a user after sampling that the test has failed due to insufficient sampling.

The invention is not limited to the detection of any particular analyte. For instance, the analyte may be of a mammalian, especially of a human origin, or of a bacterial or viral origin. More than one analyte may be detected. In the case where the device includes more than one analyte detection zone, at least a portion of the sample receiving member is preferably upstream of, or level with, at least one of the analyte detection zones.

The presence and/or amount of the analyte(s) may be indicative of any clinical, physiological or medical condition, e.g. pregnancy or fertility. The analyte(s) may, for example, be a toxin, pollutant, organic compound, protein, enzyme, peptide, microorganism, bacterium, virus, amino acid, nucleic acid, carbohydrate, hormone, steroid, vitamin or drug. In an embodiment, the analyte(s) is a hormone. In an embodiment, the analyte(s) is human chorionic gonadotropin (hCG), luteinizing hormone (LH), estrone-3-glucuronide (E3G), or a fragment or isoform thereof. These analytes are used to indicate pregnancy or the fertility status of a female.

The assay device may provide a qualitative, semi-quantitative or quantitative detection of the analyte of interest. The result of the assay can be interpreted by the user by viewing the analyte detection zone(s) and the control zone(s) if present measured by an optical or other measuring system and the result can be displayed in any known suitable form, such as via a digital display or an alternative visual signal of the assay result.

The assay device may detect more than one analyte, for instance via the inclusion of a separate detection zone for each analyte in the assay flow path. Alternatively, the assay device may comprise a plurality of separate assay flow paths; each may have its own associated sample receiving member, or a single sample receiving member may be shared between assay flow paths (e.g. if the assay flow paths are arranged side by side). The device may use a plurality of separate assay flow paths in the quantitation or semi-quantitation of a single analyte.

In use, the sample may be applied directly to the device. When the sample liquid is a bodily fluid, the device can be used to collect the liquid sample directly from a subject. For example, the device can be used to collect a mid-stream urine sample.

Alternatively, the sample may be subjected to a liquid pre-treatment step before being exposed to the assay device. The liquid pre-treatment step may comprise one or more of, but not limited to, a dilution, a liquid suspension, an extraction, filtration, a binding reaction, a biochemical reaction, a chemical reaction, a lytic reaction, a buffering or a treatment with a surfactant. Thus, as discussed above, the liquid pre-treatment step may be used in order to ensure that the sample is applied to the device in liquid form, applied with the required and controlled viscosity liquid, and/or to ensure that the analyte of interest is presented in a form which will allow the analyte to react or interact with the one or more assay reagents.

The assay device may further comprise a sampling means for obtaining a sample and transferring the sample to the sample receiving member, after any desired pre-treatment steps have been carried out. The sampling means may be adapted to receive a sample of bodily fluid from a subject.

Figure 1:
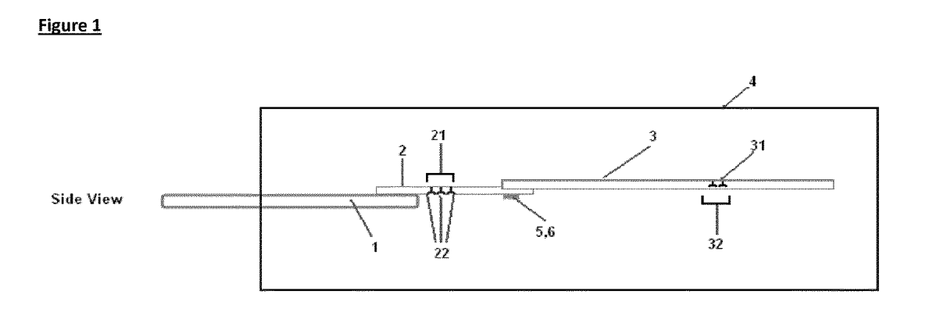
FIG. 1 illustrates a side view of an assay device in accordance with an embodiment of the invention, in which two electrodes (i.e. a pair of electrodes) are in contact with the assay flow path at the area where the first component of the assay flow path overlaps with the second component of the assay flow path.

FIG. 1 illustrates a side view of an assay device in accordance with the invention, where the sample detection element is a pair of electrodes 5,6. The assay device comprises a sample receiving member 1 fluidically connected to two components 2 and 3 defining an assay flow path. Components 2 and 3 are fluidically connected strips. Component 3 is a detection member comprising an analyte detection zone 31. The assay flow path is enclosed in a housing 4, and the sample receiving member 1 projects from the housing 4. The downstream end of the sample receiving member 1 overlaps the upstream end of strip 2, which is a conjugate pad bearing labelled mobilisable assay reagents 22 in a mobilisable reagent zone 21. The downstream end of the conjugate pad 2 overlaps the upstream end of strip 3, which bears immobilised non-labelled assay reagents 32 in an analyte detection zone 31. Two electrodes 5, 6 (i.e. a pair of electrodes) are in contact with the assay flow path, and are shown in FIG. 1 in contact with strip 2 at the area where it overlaps with strip 3.

Figure 2:
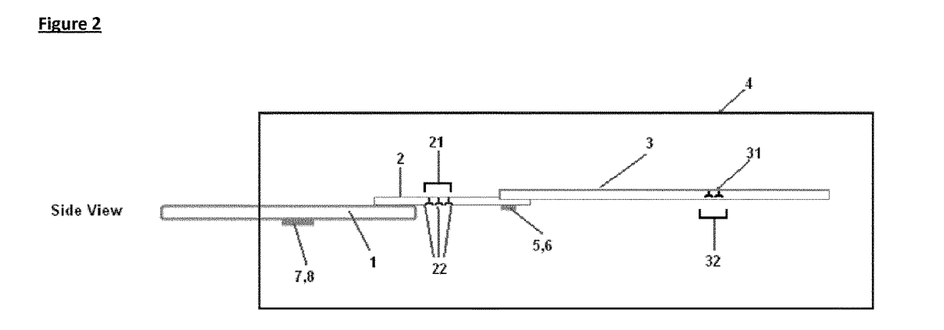
FIG. 2 illustrates a side view of an assay device in accordance with an embodiment of the invention comprising four electrodes (i.e. two pairs of electrodes). In the embodiment shown in FIG. 2, two electrodes (i.e. a pair of electrodes) are in contact with the assay flow path at the area where the first component of the assay flow path overlaps with the second component of the assay flow path, and the other two electrodes (i.e. a pair of electrodes) are in contact with the sample receiving member.

FIG. 2 illustrates a side view of an assay device in accordance with FIG. 1, where an additional pair of electrodes 7,8 are in contact with the sample receiving member 1.

Figure 3:
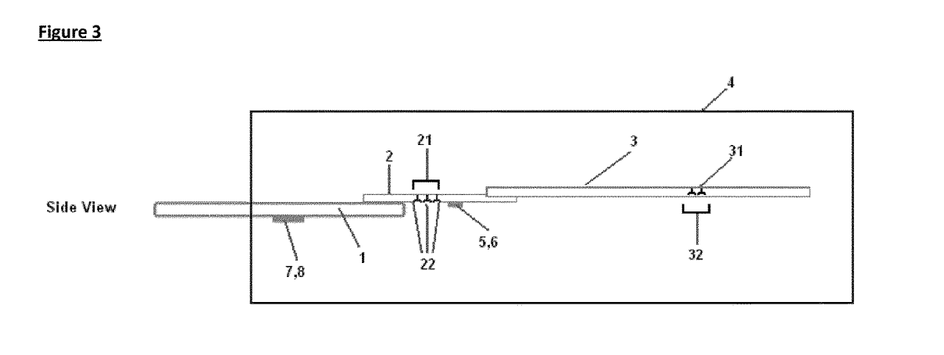
FIG. 3 illustrates a side view of an assay device in accordance with an embodiment of the invention, comprising four electrodes (i.e. two pair of electrodes). In the embodiment shown in FIG. 3, two electrodes (i.e. a pair of electrodes) are in contact with the assay flow path at the first component of the assay flow path, and the other two electrodes (i.e. a pair of electrodes) are in contact with the sample receiving member.

FIG. 3 illustrates a side view of an assay device in accordance with an embodiment of the invention, comprising four electrodes (i.e. two pairs of electrodes). In the embodiment shown in FIG. 3, a pair of electrodes 5,6 are in contact with the assay flow path in contact with strip 2 (not in the area where it overlaps with strip 3), and the other pair of electrodes 7,8 are in contact with the sample receiving member 1.

Figure 3A:
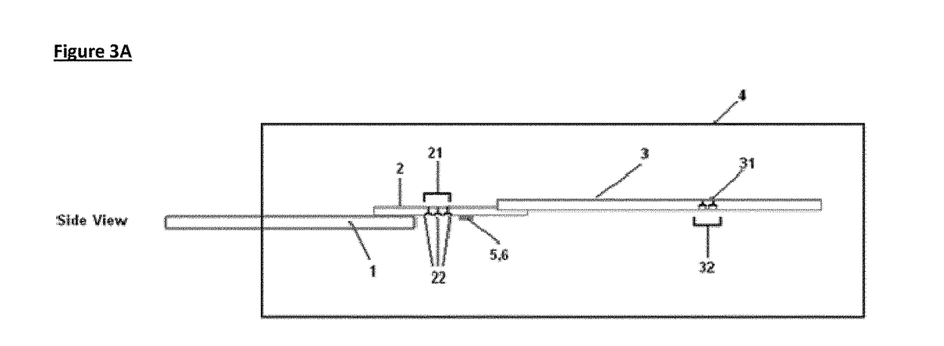
FIG. 3A illustrates a side view of an assay device in accordance with an embodiment of the invention, comprising two electrodes (i.e. one pair of electrodes). The electrodes are in contact with the assay flow path at the first component of the assay flow path.

FIG. 3A illustrates a side view of an assay device in accordance with an embodiment of the invention, comprising two electrodes (i.e. a pair of electrodes). In the embodiment shown in FIG. 3, a pair of electrodes 5,6 are in contact with the assay flow path in contact with strip 2 (not in the area where it overlaps with strip 3).

The dimensions of the assay devices illustrated in the Figures are exemplary only. The Figures are not drawn to scale. It will be appreciated that the dimensions and materials of the assay device of the invention can be varied as desired.

Unless technically inconsistent or otherwise stated, the embodiments of the invention described herein apply to both aspects of the invention mutatis mutandis.

The prior art documents mentioned herein are incorporated to the fullest extent permitted by law.

The invention will be further described and illustrated in the following non-limiting example.

EXAMPLE 1

Use of Devices of the Invention to Determine Sample Sufficiency

The following example utilised single step lateral flow pregnancy test devices, of the type described in EP 0,291,194.

The devices comprised a nylon/polyester bicomponent fibre wick as a sample receiving member, and the assay flow path was defined by a glass fibre conjugate pad overlapping a nitrocellulose strip. Blue latex-labelled anti-hCG antibody and blue-latex-labelled rabbit IgG antibody were deposited on the conjugate pad; the test zone on the nitrocellulose strip contained immobilised non-labelled anti-hCG antibody and the control zone contained immobilised non-labelled goat anti-rabbit IgG antibody. When urine containing a sufficient amount of hCG to indicate pregnancy is applied to the wick and the assay runs correctly, a blue line is expected to form in the test zone and in the control zone, caused by the immobilisation of the blue latex in those areas via a "sandwich" or other binding reaction.

Under sampling is indicated by an increased time for sample to be detected in the test window. However once flow is detected in the test window flow rate is normalised and consistent regardless of the volume of sample applied.

Varying sample volumes were applied to the device ranging from 750 ul to 1000 ul. Additional devices were dipped as per the instructions supplied with the product, (for a period of 20 seconds). The application of 1000 uls of sample to the device as well as devices dipped in the sample have been shown to produce correct running of devices to provide an accurate result. These conditions are known as the controls.

Figure 4:
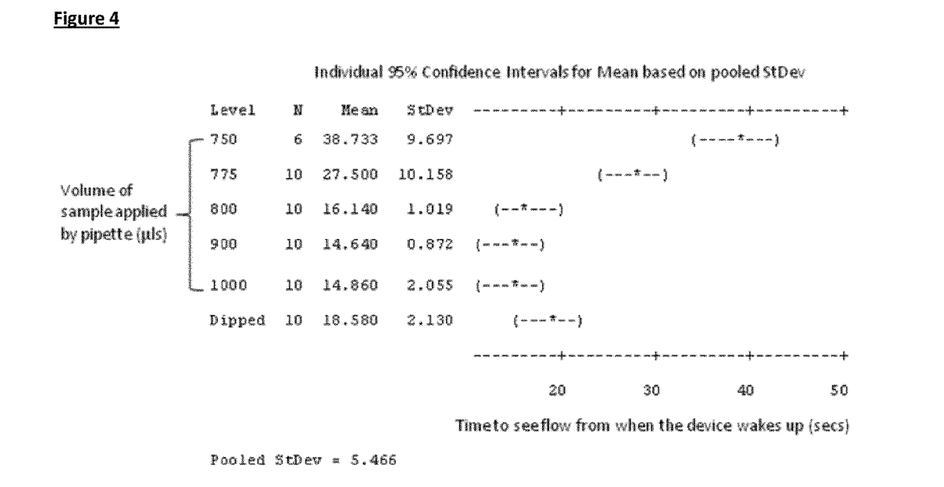
FIG. 4 shows time (in seconds) at which flow is seen from device wake up to flow being detected in the test window when applying different volumes of sample (applied using a pipette), as well as when the device is dipped (the sample receiving member is held vertically in the sample for a fixed period of time).

Devices having volumes of less than 800 ul applied to them were deemed to be susceptible to under sampling as time for the flow to reach the test window was longer than the control (1000 ul) (FIG. 4). The device determines insufficient flow of sample and highlights an error if the time taken to reach the test window is 32 seconds or more. On application of 775 uls or 750 uls of sample the time to reach the test window is reaching 32 seconds and above indicating insufficient sample resulting in a void result and a wasted device.

Figure 5:
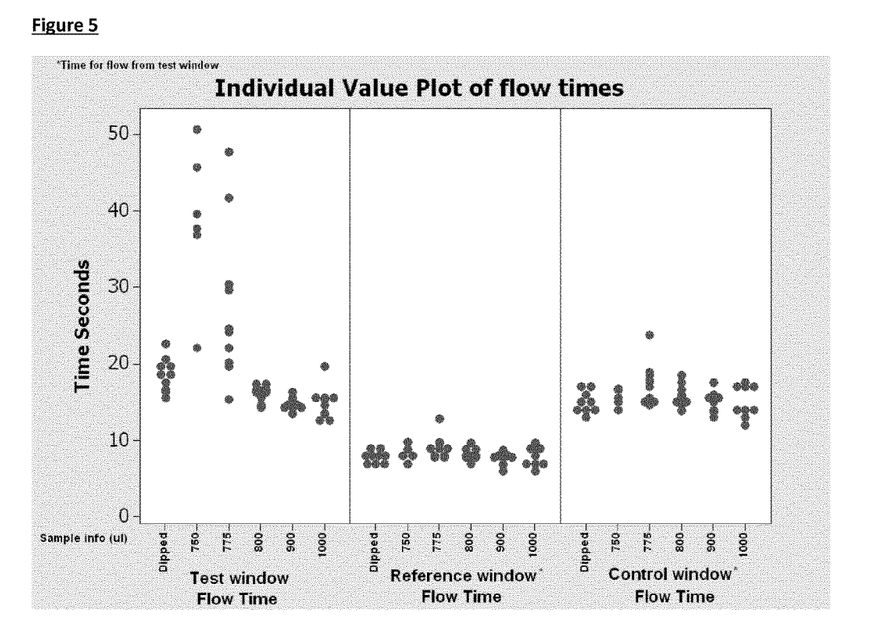
FIG. 5 is an individual value plot of flow times (in seconds), for flow to be detected at the test window (Test flow time), time for flow from the Test window (where the test line is seen) to the Reference window (in between the Test window and the Control window) (Reference flow time), and time for flow from the Test window to the Control window (where the control line is seen) (Control flow time). In these devices the flow travels from the Test window to the Reference window and onto the Control window. The Test, Reference and Control windows are all on the nitrocellulose.

FIG. 5 shows that once flow has reached the test window, the time for flow to reach the Reference and Control windows is normalised.

Detection of sample by electrodes in contact with component 2 downstream of the sample receiving member indicates sample has flowed from the sample receiving member to component 2 of the assay at the interface point (as shown in FIGS. 1 and 2).

The position of the electrodes on component 2 dictate the format used (FIGS. 1 to 3).

Figure 6:
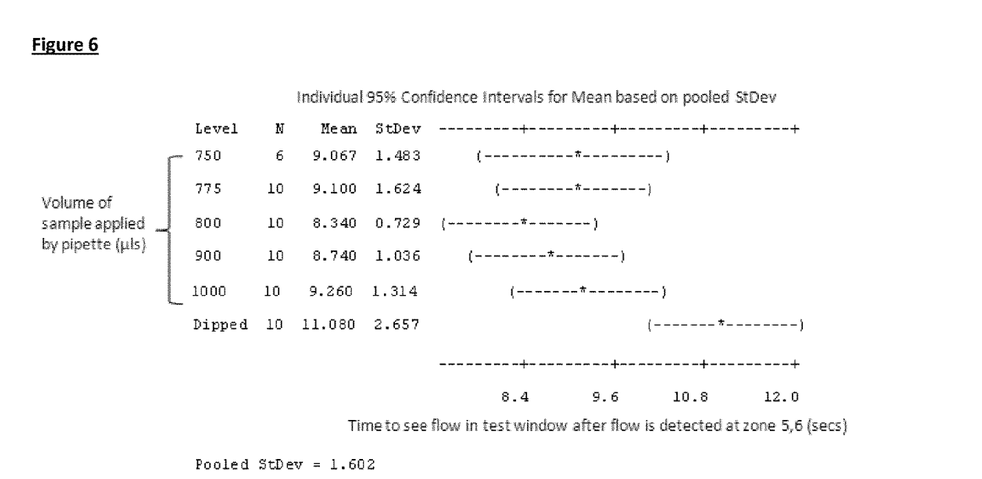
FIG. 6 shows time (in seconds) at which flow is seen in the Test window after flow is detected at electrodes 5,6 when the devices are tested with different volumes of sample applied (using a pipette), as well as when the device is dipped (the sample receiving member is held vertically in the sample for a fixed period of time).

Electrodes at the overlap zone between components 2 and 3 (location 5,6) as shown in FIGS. 1 and 2 indicate the fluid has flowed to a point where the assay will proceed to completion as it indicates sufficient sample is present. (FIG. 6). Once flow is detected by the electrode (5,6) flow is normalised downstream of this point as all volumes tested take between ~8 and ~16 seconds for flow to reach the test window (from detection of flow at location 5,6).

Figure 7:
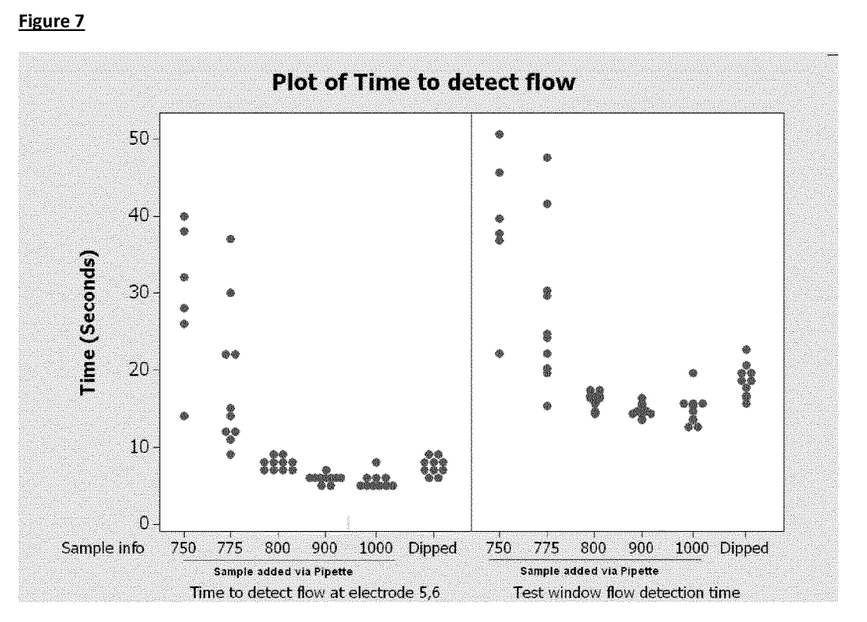
FIG. 7. The left hand side of this graph shows a plot of time (in seconds) to detect flow at electrodes 5,6. The right hand side of the graph shows a plot of time (in seconds) to detect flow at the Test window. Various volumes of sample were applied to the devices and some devices were dipped as described for FIGS. 4 to 6.
Figure 8:
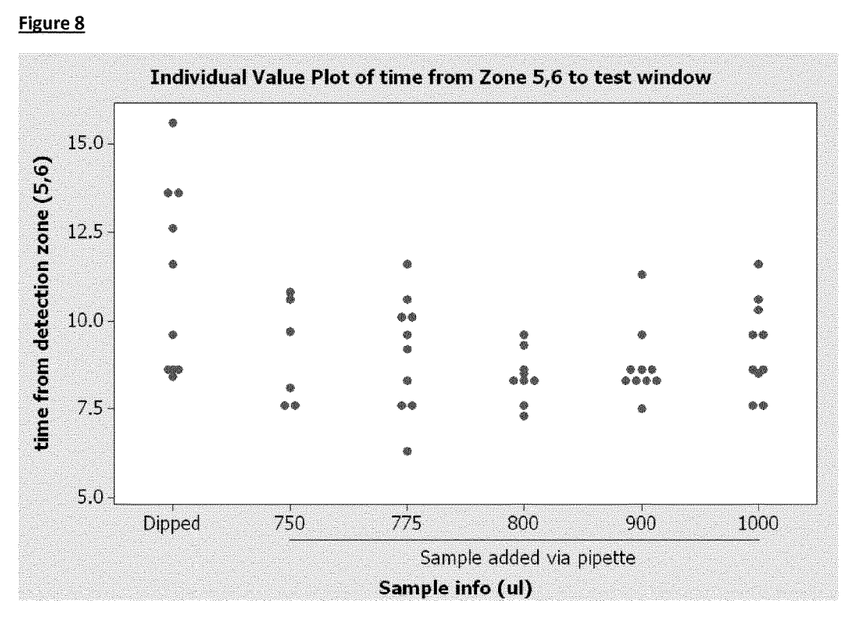
FIG. 8 shows time (in seconds) to detect flow at test window from electrode position 5,6. Various volumes of sample were applied to the devices and some devices were dipped as described for FIGS. 4 to 6.

The left hand side of the graph of FIG. 7 demonstrates the time at which flow was seen at the electrode in contact with component 2 at the overlap with component 3 and is representative of the time at which flow is seen in the test window (the graph on the right hand side of FIG. 7) which is nominally 10 seconds later (FIG. 8).

This can be used independently (FIG. 1) to demonstrate sufficient fluid has been received for the assay to run to completion and provide an accurate result. Alternatively electrodes 5, 6 can be used in combination with electrodes 7, 8 positioned on the sample receiving member to indicate when sample is initially added and wakes up the device and the electrodes 5,6 to indicate sufficient sample has been added (FIG. 2)

Position of electrodes 5,6 on component 2 but not at the overlap between components 2 and 3 (FIG. 3) and in combination with additional electrodes 7,8 can indicate sufficient sample being present. In this embodiment, the time between detecting sample at electrodes 7,8 and electrodes 5,6 can be used to determine whether sufficient sample has been applied to the device. A short time of flow between electrodes 7,8 and 5,6 can be used to indicate sufficient sample has been applied to the device. In this way the user can be alerted to stop sampling earlier. Conversely, a longer time of flow between the two sets of electrodes can be used to indicate insufficient sample. The user may carry on sampling until flow reaches electrodes 5,6 or the user may be informed that they have sampled insufficiently via the display means (LCD).

In summary, the results presented herein demonstrate that devices in accordance with the present invention are useful to indicate that a sufficient amount of sample has been added to the device.

The invention claimed is:

1. An assay device for detecting an analyte in a fluid sample, comprising:
   a sample receiving member, which is fluidically connected to at least two components defining an assay flow path, at least one of which is a detection member comprising an analyte detection zone; and
   a sample detection element that is in contact with the assay flow path, located upstream of the analyte detection zone and is adapted to detect fluid at a particular point along the assay flow path; the sample detection element comprising a pair of electrodes; and an indication system electrically coupled to the sample detection element and adapted to provide feedback to a user during a sampling event as a result of sample fluid arriving at the sample detection element to indicate that sufficient sample is applied to the device.

2. The assay device of claim 1, wherein the analyte detection zone contains one or more immobilised assay reagents and the components defining the assay flow path bear one or more mobilisable assay reagent(s) in a mobilisable reagent zone upstream from the analyte detection zone.

3. The assay device of claim 1, wherein the components defining the assay flow path comprise at least two fluidically connected porous materials.

4. The assay device of claim 3, wherein the analyte detection zone contains one or more immobilised assay reagents and the components defining the assay flow path bear one or more mobilisable assay reagent(s) in a mobilisable reagent zone upstream from the analyte detection zone, and wherein the mobilisable assay reagent(s) are borne by a first porous material, and the immobilised assay reagents are borne by a fluidically connected second porous material.

5. The assay device of claim 1, wherein the sample detection element is the pair of electrodes.

6. The assay device of claim 1, wherein the first component and the second component of the assay flow path at least partially overlap.

7. The assay device of claim 1, wherein the sample detection element is in contact with the first component of the assay flow path.

8. The assay device of claim 6, wherein the sample detection element contacts the first component of the assay flow path in the area where the first component and the second component of the assay flow path overlap.

9. The assay device of claim 8, wherein the pair of electrodes pierce the first component of the assay flow path and contact the second component of the assay flow path.

10. The assay device of claim 6, wherein the sample detection element contacts the first component of the assay flow path in the area where the first component and the second component of the assay flow path do not overlap.

11. The assay device of claim 1, wherein the sample detection element is in contact with the second component of the assay flow path.

12. The assay device of claim 1, wherein the assay device comprises the pair of electrodes and no other electrodes.

13. The assay device of claim 9, further comprising a second pair of electrodes in contact with the sample receiving member.

14. The assay device of claim 13, wherein the second pair of electrodes wakes up the device and the first pair of electrodes indicates sample sufficiency.

15. The assay device of claim 14, which is adapted to monitor the time taken for sample fluid to flow from the second pair of electrodes to the first pair of electrodes.

16. The assay device of claim 1, wherein the indication system is adapted to indicate that sufficient sample has been applied to the assay device visually, aurally and/or tactilely.

17. The assay device of claim 16, wherein the indication system includes an LED.

18. The assay device of claim 1, wherein the pair of electrodes are part of an electrical circuit that is connected to the indication system.

19. The assay device of claim 1, wherein the sample receiving member is porous.

20. The assay device of claim 19, wherein the sample receiving member is a wick.

21. The assay device of claim 1, wherein the assay flow path further comprises a control zone.

22. The assay device of claim 1, adapted to detect an analyte in a sample that has a viscosity of ≤2 mPa·s, ≤1.5 mPa·s, or ≤1 mPa·s at 25 °C.

23. The assay device of claim 1, wherein the sample is urine.

24. A method of alerting a user to the fact that a sufficient sample has been applied to an assay device, comprising:
(a) exposing the assay device of claim 1 to a fluid sample; and
(b) alerting the user to the fact that a sufficient sample has been obtained.

25. The method of claim 24, comprising:
(a) holding the assay device in the urine stream of a user; and
(b) alerting the user to the fact that a sufficient sample has been obtained, whilst the user continues to sample from the urine stream.

26. The assay device of claim 17, wherein the LED is located at a downstream end of the assay device.

27. The method of claim 24, comprising:
(a) dipping the assay device into a urine sample held in a container; and
(b) alerting the user to the fact that a sufficient sample has been obtained, whilst the user continues to sample from the urine stream.

28. A method of alerting a user to the fact that an insufficient sample has been applied to an assay device, comprising:
(a) exposing the assay device of claim 1 to a fluid sample; and
(b) alerting the user to the fact that the test has failed due to insufficient sampling.

* * * * *